United States Patent [19]  
Isak et al.

[11] Patent Number: 5,354,883
[45] Date of Patent: Oct. 11, 1994

[54] PREPARATION OF E-OXIME ETHERS OF PHENYLGLYOXYLIC ESTERS

[75] Inventors: Heinz Isak, Mutterstadt; Michael Keil, Freinsheim; Bernd Wolf, Fussgoenheim; Horst Wingert, Mannheim, all of Fed. Rep. of Germany

[73] Assignee: BASF Aktiengesellschaft, Ludwigshafen, Fed. Rep. of Germany

[21] Appl. No.: 14,149

[22] Filed: Feb. 5, 1993

[30] Foreign Application Priority Data

Feb. 5, 1992 [DE] Fed. Rep. of Germany ....... 4203170

[51] Int. Cl.$^5$ .......................................... C07C 229/00
[52] U.S. Cl. .................................................... 560/35
[58] Field of Search ......................................... 560/35

[56] References Cited

U.S. PATENT DOCUMENTS

| | | | |
|---|---|---|---|
| 4,829,085 | 5/1989 | Wenderoth et al. | 560/35 |
| 4,999,042 | 3/1991 | Anthony et al. | 560/35 |
| 5,112,862 | 5/1992 | Wenderoth et al. | 560/35 |
| 5,116,866 | 5/1992 | Wenderoth et al. | 560/35 |
| 5,221,762 | 6/1993 | Wingert et al. | 560/35 |

FOREIGN PATENT DOCUMENTS

| | | |
|---|---|---|
| 0254426 | 3/1991 | European Pat. Off. . |
| 0400417 | 9/1992 | European Pat. Off. . |
| 0386561 | 11/1992 | European Pat. Off. . |

OTHER PUBLICATIONS

CA108(71): 186546j, Fernandez et al; "The Role of Acids in the Beckman Rearrangement of (−)-1R, trans) —p— Menthan -3-One(E)-Oxime", *J. Chem. Res. Symp.*, (10), 340–1. 1987. Abstract only.

*Primary Examiner*—Marianne M. Cintins
*Assistant Examiner*—Keith MacMillan
*Attorney, Agent, or Firm*—Oblon, Spivak, McClelland, Maier & Neustadt

[57] ABSTRACT

E-Oxime ethers of phenylglyoxylic esters of the formula I

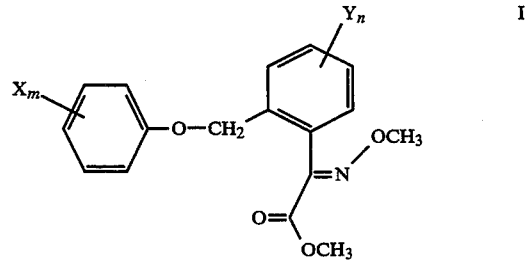

X, Y=halogen, alkyl, alkoxy, CF$_3$, C(=NOR)R (R=alkyl or alkenyl) are prepared by reacting oximes of the formula II

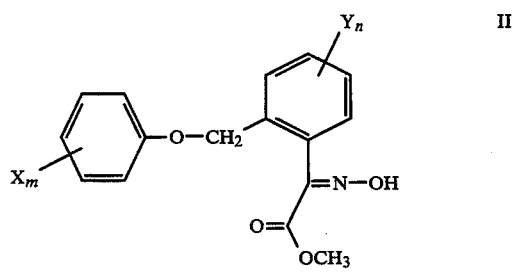

with a methylating agent in an organic diluent, and E-oximes of phenylglyoxylic esters of the formula II are prepared by isomerizing the E/Z-oximes.

4 Claims, No Drawings

PREPARATION OF E-OXIME ETHERS OF PHENYLGLYOXYLIC ESTERS

The present invention relates to a process for preparing E-oxime ethers of phenylglyoxylic esters of the formula I

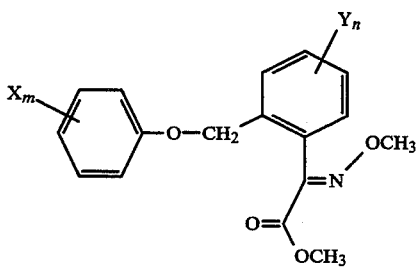

where
X and Y are identical or different and each is halogen, $C_1$-$C_4$-alkyl, $C_1$-$C_4$-alkoxy, trifluoromethyl, or 1-$C_1$-$C_5$-alkyl ($C_2$-$C_5$-alkenyl)hydroxyimino-$C_1$-$C_5$-alkyl ($C_2$-$C_5$-alkenyl) and 1-$C_1$-$C_5$-alkyl ($C_2$-$C_5$-alkenyl)hydroxyimino,
m is an integer from 0 to 4,
n is an integer from 0 to 3.

The preparation of oxime ethers of the formula I type by reacting glyoxylic esters with O-methylhydroxylamine hydrochloride has been disclosed (cf., for example, EP-A 253 213 and EP-A 254 426), there being formation of equimolar amounts of hydrogen chloride as by-product. However, a disadvantage of this process is that it gives mixtures of E and Z isomers of the oxime ethers which can be separated industrially only at relatively great expense. This process gives the preferred isomer with the E configuration at the oxime linkage only in very small amounts.

Another process which has been described (EP 493,711 in which the preparation is followed by an isomerization to give a high proportion of the required isomer with the E configuration. However, disadvantages of this process are, on the one hand, the large excess of hydrogen chloride required for the isomerization and, on the other hand, the strain on the economics of the process owing to the use of methoxylamine hydrochloride, which is difficult to obtain.

It is an object of the present invention to make it easier to obtain the compounds I.

We have found that this object is achieved by a process for preparing E-oxime ethers wherein E-oximes of phenylglyoxylic esters of the formula IIa are converted with a base in the presence of an organic diluent into the corresponding salt and the latter is reacted with an alkylating agent of the formula III.

It is known from Houben-Weyl, Methoden der Organischen Chemie, Volume 10/4, pages 217 to 223, that reaction of ketoximes with an alkylating agent may lead to bonding of alkyl both to the nitrogen and to the oxygen of the oxime. The result in the first case is a nitrone and in the second case is an oxime ether. The reaction usually gives both products. Methods which can be used to obtain exclusively these products are described but either they cannot be carried out on the industrial scale or they give an inadequate yield of the required substance. Thus, it is stated in Houben-Weyl (loc. cit., page 223) that the dried silver salt of the particular oxime can be reacted with alkyl iodide in the presence of silver oxide in absolute ether or alcohol. This procedure is time-consuming and uneconomic on the industrial scale. It is also possible to methylate cyclohexanone oxime with dimethyl sulfate in aqueous sodium hydroxide solution (Coll. Czech. Chem. Comm. 14 (1949) 561-563). However, the yield of product, which is still impure, is only 37% of theory. The yield when the oxime is reacted with allyl bromide is likewise only 35.9% of theory.

In addition, EP 23560 discloses a process for preparing o-substituted ketoximes. However, this publication does not describe the oximes of phenylglyoxylic esters.

Halogen is, for example, fluorine, chlorine, bromine or iodine; $C_1$-$C_4$-alkyl is, for example, methyl, ethyl, propyl (n-propyl, isopropyl) or butyl; $C_1$-$C_4$-alkoxy is, for example, methoxy, ethoxy, propoxy or butoxy. 1-$C_1$-$C_5$-alkyl ($C_2$-$C_5$-alkenyl)hydroxyimino-$C_1$-$C_5$-alkyl($C_2$-$C_5$-alkenyl) is, for example, 1-methoxyiminoethyl($CH_3ON$=$CCH_3$—) or methoxyiminomethyl($CH_3ON$=$CH$—).

The reaction according to the invention is generally carried out at from $-20°$ to $+100°$ C. preferably from $0°$ to $80°$ C., especially at $20°$-$80°$ C., under atmospheric or superatmospheric pressure, continuously or batchwise.

The starting materials are reacted in the stoichiometric amounts or with an excess, expediently in amounts of from 1 to 2, in particular from 1.05 to 1.5, mole of III and from 1 to 1.5 mole of base per mole of II. Organic diluents which can be used are aprotic dipolar solvents, which are defined as solvents whose molecules have a pronounced dipole moment but no hydrogen atoms able to form hydrogen bonds. Solvents of this type have dielectric constants above 15. Concerning the definition of aprotic dipolar solvents, reference is made to A. J. Parker, Chem. Rev. 69 (1969) 1-32, especially page 2. Thus, examples of suitable aprotic dipolar solvents are sulfoxides such as dimethyl sulfoxide, diethyl sulfoxide, dimethyl sulfone, diethyl sulfone, methyl ethyl sulfone, tetramethylene sulfone; nitriles such as acetonitrile, benzonitrile, butyronitrile, isobutyronitrile, m-chlorobenzonitrile; N,N-disubstituted carboxamides such as dimethylformamide, tetramethylurea, N,N-dimethylbenzamide, N,N-dimethylacetamide, N,N-dimethylphenylacetamide, N,N-dimethylcyclohexanecarboxamide, N,N-dimethylpropionamide and homologous piperidides, morpholides and pyrrolidides; corresponding N,N-diethyl, N,N-dipropyl, N,N-diisopropyl, N,N-diisobutyl, N,N-dibenzyl, N,N-diphenyl, N-methyl-N-phenyl, N-cyclohexyl-N-methyl and N-ethyl-N-tert-butyl compounds, N-methylformanilide, N-ethylpyrrolidone, N-butylpyrrolidone, N-ethyl-2-piperidone, N-methylpyrrolidone; hexamethylphosphoric triamide; and corresponding mixtures. Dimethylacetamide, N-methylpyrrolidone, dimethylformamide, dimethyl sulfoxide and tetramethylene sulfone are preferred, and N-methylpyrrolidone and dimethylformamide are particularly preferred.

One variant of the process comprises reacting the oxime salt further without removing the diluent.

We have also found that the E-oxime of the formula IIa is obtained when a mixture of the E-oxime of the formula IIa and the Z-oxime of the formula IIb is treated with a catalyst in an organic diluent. One example of a catalyst is an acid. An organic diluent is, for example, an aromatic hydrocarbon or a chlorinated hydrocarbon or an alcohol.

Suitable solvents are preferably aromatic hydrocarbons such as benzene, toluene and o-, m- and p-xylene, chlorinated hydrocarbons such as methylene chloride, and alcohols such as methanol and ethanol. Methanol is particularly preferred.

Particularly suitable acids are mineral acids, for example perchloric acid, sulfuric acid, phosphoric acid and hydrohalic acids such as hydrogen chloride, aliphatic sulfonic acids such as trifluoromethanesulfonic acid, aromatic sulfonic acids such as p-toluenesulfonic acid and halogenated alkanecarboxylic acids such as trifluoroacetic acid. Gaseous hydrogen chloride is particularly preferred.

The amount of acid used is normally from 0.01 to 10, in particular from 0.01 to 5, times the molar amount of the mixture of IIa and IIb.

The isomerization is generally carried out at from $-20°$ to $100°$ C., in particular from $20°$ to $80°$ C.

The rearrangement of the oximes takes a certain time which depends on the temperature and, in particular, the amount of acid and is about 1–90 hours, preferably 2–10 hours.

As a rule, all the steps in the process can be carried out under atmospheric pressure or under the autogenous pressure of the particular system, up to about 5 bar. A higher or lower pressure is also possible but generally has no advantages.

The process according to the invention can be carried out either batchwise or continuously. In the latter case the reactants are passed, for example, through a tubular reactor or cascades of stirred vessels.

We have also found that a mixture of the E-oxime of the formula IIa and the Z-oxime of the formula IIb is obtained when a corresponding phenylglyoxylic ester of the formula IVa is reacted with hydroxylamine or one of its acid addition salts.

The hydroxylamine is employed either in the form of an acid addition salt or as the free base, it being possible to liberate the unprotonated compound from the salt by adding a strong base. Suitable salts of hydroxylamine are the salts with monobasic to tribasic acids such as, in particular, hydrochloric acid and sulfuric acid.

The reaction is carried out, for example, in the presence of a solvent or diluent.

Suitable solvents are preferably aromatic hydrocarbons such as benzene, toluene and o-, m- and p-xylene, chlorinated hydrocarbons such as methylene chloride, and alcohols such as methanol and ethanol. Methanol is particularly preferred.

The ratios of the amounts of the starting materials are not critical; it is expedient to employ stoichiometric amounts of starting compounds unless an excess of one of the components, e.g. 10 mol %, is advisable.

The reaction is normally carried out at from $0°$ to $100°$ C., preferably from $20°$ to $80°$ C.

We have also found that the E-oximes of the formula IIa are obtained when a phenylglyoxylic ester of the formula IVa

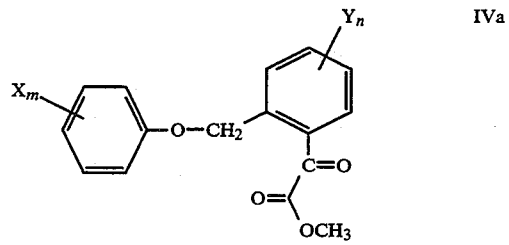

or a ketal of a phenylglyoxylic ester of the formula IVb

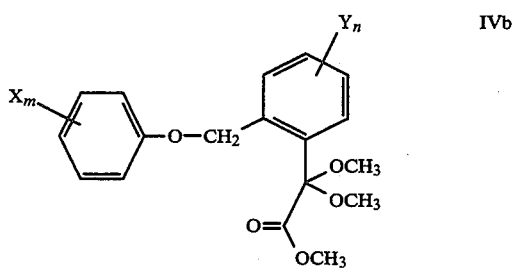

or an amide of the formula IVc

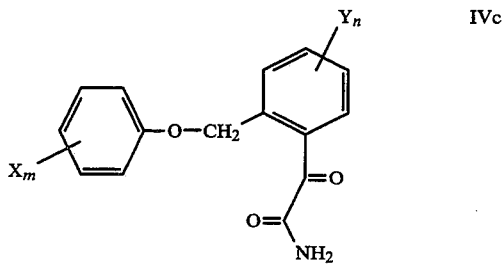

or a mixture of compounds IVa, b and c is reacted with hydroxylamine or one of its acid addition salts and, at the same time or subsequently, treated with a catalyst in an organic diluent.

The phenylglyoxylic esters, ketals and amides of the formula IVa-c used as starting materials can be obtained, for example, by the process described in EP Application 91121148.0.

Both the phenylglyoxylic esters IVa and the derivatives IVb and IVc or mixtures of these compounds are suitable as starting materials for the process according to the invention. It is possible in particular to convert the mixture of crude products IVa-c obtained in a Pinnet reaction without further purification into the E-oxime of the formula IIa by this process.

The hydroxylamine is employed either in the form of an acid addition salt or as the free base, it being possible to liberate the unprotonated compound from the salt by adding a strong base. Suitable salts of hydroxylamine are the salts with monobasic to tribasic acids such as, in particular hydrochloric acid and sulfuric acid.

Suitable solvents are preferably aromatic hydrocarbons such as benzene, toluene and o-, m- and p-xylene, chlorinated hydrocarbons such as methylene chloride, and alcohols such as methanol and ethanol. Methanol is particularly preferred.

The ratios of the amounts of the starting materials are not critical; it is expedient to employ stoichiometric amounts of starting compounds unless an excess of one of the components, e.g. 10 mol %, is advisable.

The reaction is normally carried out at from 0° to 100° C., preferably from 20° to 80° C.

One variant of the process comprises reacting the mixture of compounds IVa and IVb obtained in a Pinner reaction, without separation from the reaction mixture, with hydroxylamine or one of its acid addition salts.

The oximes of phenylglyoxylic esters are usually obtained as mixtures of isomers in which the oxime moiety is partly in the E and partly in the Z configuration. Rearrangement of the oximes to the E configuration is brought about by treatment with an acid.

For this purpose, the crude solution of the oximes can be previously concentrated or diluted further. If required, the rearrangement can also be carried out in a two-phase system composed of water/acid and an organic solvent such as dichloromethane. However, it is expedient to treat the resulting crude solution of the oxime, without further concentration or dilution, directly with the acid. Particularly suitable acids are mineral acids, for example perchloric acid, sulfuric acid, phosphoric acid and hydrohalic acids such as hydrogen chloride, aliphatic sulfonic acids such as trifluoromethanesulfonic acid, aromatic sulfonic acids such as p-toluenesulfonic acid and halogenated alkanecarboxylic acids such as trifluoroacetic acid. Gaseous hydrogen chloride is particularly preferred.

The amount of acid used is normally from 0.01 to 10 times, in particular from 0.01 to 5 times, the molar amount of the mixture of IIa and IIb.

The isomerization is generally carried out at from −20° to 100° C., in particular from 20° to 80° C.

The rearrangement of the oximes takes some time which depends on the temperature and, in particular, on the amount of acid and is about 1–90 hours, preferably 2–10 hours.

As a rule, all the steps in the process can be carried out under atmospheric pressure or under the autogenous pressure of the particular system, to about 5 bar. A higher or lower pressure is also possible but generally has no advantages.

The process according to the invention can be carried out either batchwise or continuously. In the latter case, the reactants are passed, for example, through a tubular reactor or through cascades of stirred vessels.

The process according to the invention can be used successfully to synthesize the E-oximes of phenylglyoxylic esters, especially the compounds where X and Y have, independently of one another, the following meanings:

halogen such as fluorine, chlorine and bromine;
branched or unbranched $C_1$–$C_4$-alkyl such as methyl, ethyl, isopropyl and n-butyl, especially methyl and ethyl;
$C_1$–$C_4$-alkoxy such as methoxy, ethoxy, 1-methylethoxy and n-propoxy;
trifluoromethyl.

The E-oximes of the formula II can, surprisingly, be obtained in high yield and excellent purity by the process according to the invention. In view of the prior art, by contrast, the same difficulties as occur in the known processes were to be expected with the process. In particular, it was by no means possible to predict that isomerization under acid conditions predominantly forms the E isomer, because in the known synthetic methods in which hydroxylamine hydrochloride is used there is formation of equimolar amounts of hydrogen chloride during the reaction without preferential production of one isomer. In addition, decomposition of the oxime would have been expected on treatment of the crude products with acid.

The process according to the invention has a number of advantages:
- it can be carried out on the industrial scale in a very straightforward manner;
- the salts of hydroxylamine can be employed as aqueous solutions;
- the phenylglyoxylic esters IVa can be employed as crude product from the previous stage because the dimethyl ketal of the phenylglyoxylic ester which is present as impurity is surprisingly also converted into the required E-oxime.

The E-oxime ethers of the formula I are described in EP 253 213 and EP 254 426 as crop protection agents.

We have also found that E-oxime ethers of the formula I are obtained when nitrones of the formula V

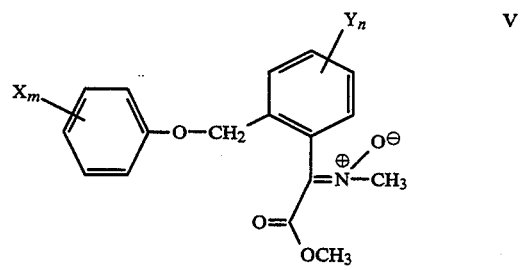

in which the substituents have the meanings specified in claim 1,
a) are reacted with O-methylhydroxylamine or one of its acid addition salts. The nitrones of the formula V may be formed as by-products in the reaction of oximes of the formula IIa with alkylating agents of the formula III.

The reaction is generally carried out at from −20° to +100° C., preferably from 0° to 80° C., in particular at 20°–80° C., under atmospheric or superatmospheric pressure, continuously or batchwise.

The methylhydroxylamine is employed either in the form of an acid addition salt or as the free base, it being possible to liberate the unprotonated compound from the salt by adding a strong base. Suitable salts of methylhydroxylamine are the salts with monobasic to tribasic acids such as, in particular, hydrochloric acid and sulfuric acid.

The reaction is carried out, for example, in the presence of a solvent or diluent.

Suitable solvents are preferably aromatic hydrocarbons such as benzene, toluene and o-, m- and p-xylene, chlorinated hydrocarbons such as methylene chloride, and alcohols such as methanol and ethanol. Methanol is particularly preferred.

The ratios of the amounts of the starting materials are not critical; it is expedient to employ stoichiometric amounts of starting compounds unless an excess of one of the components, e.g. 10 mol %, is advisable.

We have also found that E-oximes of the formula IIa are obtained when nitrones of the formula V where the substituents have the meanings specified in claim 1
b) are reacted with hydroxylamine or one of its acid addition salts. The nitrones of the formula V may be formed as by-products in the reaction of oximes of the formula IIa/IIb with alkylating agents of the formula III.

The reaction is generally carried out at from −20° to 100° C., preferably from 0° to 80° C., in particular at 20°–80° C., under atmospheric or superatmospheric pressure, continuously or batchwise.

Organic solvents which can be used are aprotic dipolar and protic solvents. Alcohols are preferred. Methanol or a methanol/water mixture is particularly preferred.

The hydroxylamine is employed either in the form of an acid addition salt or as the free base.

The ratios of the amounts of starting materials are not critical; it is expedient to employ stoichiometric amounts of starting compounds unless an excess of one of the components, e.g. 10–20 mol %, is advisable.

We have also found that glyoxylic esters of the formula IVa/IVb are obtained when nitrones of the formula V where the substituents have the meanings specified in claim 1 c1) are reacted with an alcohol or alcoholate, particularly preferably methanol or methanolate, followed by aqueous work-up, c2) or reacted with an acid in the presence of an organic diluent, preferably of an alcohol, particularly preferably methanol.

The reactions are generally carried out at from −20° to 100° C., in particular at 20°–70° C., under atmospheric or superatmospheric pressure.

The ratios of the amounts of the starting materials are not critical; it is expedient to employ stoichiometric amounts of starting compounds unless an excess of one of the components, e.g. 30–50%, is advisable.

Particularly suitable acids are mineral acids, for example perchloric acid, sulfuric acid, phosphoric acid and hydrohalic acids such as hydrogen chloride, aliphatic sulfonic acids such as trifluoromethanesulfonic acid, aromatic sulfonic acids such as p-toluenesulfonic acid and halogenated alkanecarboxylic acids such as trifluoroacetic acid. Gaseous hydrogen chloride is particularly preferred.

The reaction of the oximes takes a certain time which depends on the temperature and, in particular, on the amount of acid and is about 1–90 hours, preferably 2–10 hours.

As a rule, it is possible for all the steps in the process to be carried out under atmospheric pressure or under the autogenous pressure of the particular system, to about 5 bar. A higher or lower pressure is also possible but generally has no advantages.

The process can be carried out either batchwise or continuously. In the latter case, the reactants are passed, for example, through a tubular reactor or cascades of stirred vessels.

EXAMPLE 1

Preparation of methyl E-2-(2-methylphenoxymethyl)phenylglyoxylate O-methyl oxime a) 11.96 g (40 mmol) of methyl E-2-(2-methylphenoxymethyl)phenylglyoxylate oxime are dissolved in 40 ml of dimethylformamide and, after addition of 2.38 g (43 mmol) of sodium methylate, stirred for 15 min. The mixture is then cooled to 0°–5° C. and 3.03 g (60 mmol) of gaseous methyl chloride are passed in.

The mixture is then left to stir at RT (room temperature 20° C.) for 1 h.

High pressure liquid chromatography (HPLC) check: 84% product, 11% nitrone (% by weight)

0.5 g of sodium methylate is added to convert the nitrone. The crude product is concentrated, taken up in methyl tert-butyl ether (MTBE), washed 3x with water, dried over magnesium sulfate and evaporated.

Yield: 10.1 g (81%)
Purity: >95% (HPLC)

b) Example with DMS (dimethyl sulfate) (toluene)

15.0 g (47 mmol) of methyl E-2-(2-methylphenoxymethyl)phenylglyoxylate oxime are dissolved in 100 ml of toluene and, after addition of 9.45 g of 30% strength sodium methylate solution, stirred for 15 min. Then 5.2 ml (55 mmol) of dimethyl sulfate are added and the mixture is stirred for about 8 h. It is finally concentrated, taken up in 20 ml of diethyl ether, washed 3 x with water, dried over magnesium sulfate and again concentrated.

Yield: 14.1 g (96%)
Purity: above 87% c) 19 ml of a solution of sodium methylate (0.105 mol) in methanol (30% strength) are added dropwise to a solution of 29.9 g (0.1 mol) of methyl E-2-(2-methylphenoxymethyl)phenylglyoxylate oxime in 100 ml of 1-methyl-2-pyrrolidone at 25° C. and the mixture is stirred at this temperature for 15 minutes. The methanol is removed by distillation under reduced pressure and then the reaction solution is cooled to −5° C. and 7.6 g (0.15 mol) of methyl chloride are passed in. The mixture is then stirred at 0° to +5° C. for 5 hours. The solvent is removed by distillation under reduced pressure, and the residue is taken up in diethyl ether and water. After phase separation, the organic phase is extracted 3x with water, dried over sodium sulfate and concentrated. The residue (29 g) contains 85% of the required O-methyl oxime in addition to 11% of methyl 2-(2-methylphenoxymethyl)phenylglyoxylate methylnitrone. The pure O-methyl oxime can be obtained by recrystallization from methanol.

EXAMPLE 2

Methyl E/Z-2-(2-methylphenoxymethyl)phenylglyoxylate oxime

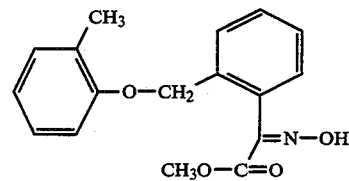

a) 5.68 g (20 mmol) of methyl 2-(2-methylphenoxymethyl)phenylglyoxylate are dissolved in 25 ml of methanol, and 1.53 g (22 mmol) of hydroxylamine hydrochloride are added. The reaction mixture is refluxed for 2 h. The crude product is freed of solvent, dissolved in about 100 ml of MTBE, washed 3x with 20 ml of water, dried over sodium sulfate and evaporated to dryness.

Yield: 5.90 g=100% of theory
Purity: 92.6% (cis:trans=75:25)

b) 45.2 g (0.18 mol) of 2-(2-methylphenoxymethyl)benzoyl cyanide are added to 27 ml of methanol, 135 ml of toluene and 3.6 g of water at −5° C. 27 g of gaseous hydrogen chloride are passed in at −10° C. to −5° C., and the mixture is warmed to 25° C. and stirred at this temperature for 15 hours. The resulting mixture [25% of methyl 2-(2-methylphenoxymethyl)phenylglyoxylate, 63% of 2-(2-methylphenoxymethyl)phenylglyoxylamide] is mixed with 121.5 ml of methanol and 12.5 g (0.18 mol) of hydroxylammonium chloride and stirred at 64° C. for 7 hours. After cooling to room temperature, the precipitated ammonium chloride is filtered off and the mother liquor is concentrated. The residue (54 g) contains 72% of E-oxime and 12% of Z-oxime.

It was possible to obtain the pure isomers by column chromatography.

Isomers: Methyl E-2-(2-methylphenoxymethyl)phenylglyoxylateoxime, melting point 115° C. Methyl Z-2-(2-methylphenoxymethyl)phenylglyoxylate oxime, melting point 105° C.

The following attempts to prepare the same compound were carried out under similar conditions.

TABLE

| | | Isomerization of E/Z-oximes | | | | |
|---|---|---|---|---|---|---|
| E/Z oxime ratio in the mixture | Experimental conditions | Solvent | Reaction temperature | Reaction time | Isomer ratio | prep. yield (E/Z) |
| 28.4 g (55.9:35.3) (0.1 mol) | Hydrogen chloride: addition of 3.6 g of HCl at 25° C. (0.1 mol) | Methanol | Reflux | 8 h | 85:8 | 80% (97:2) |
| 2.84 g (47.8/43.8) (0.01 mol) | Thermal: Heating from 100° C. to 160° | none | — | 4 h | 60.7:21 | — |
| 2.84 g (8.5/87.9) (0.01 mol) | UV light: with Hg lamp | $CH_2Cl_2$ | Reflux | 8 h | 26.1:65 | — |
| 2.84 g (8.5/87.9) (0.01 mol) | UV light with catalyst: Thiophenol | Toluene | Reflux | 8 h | 11.8:81.5 | — |
| 2.8 kg (63.5/22.1) (0.01 mol) | With acids: p-Toluenesulfonic acid (0.1 mol) | Methanol | Reflux | 2 days | 38.5:9.4 | — |
| 2.84 g (0.01 mol) | Acetic acid (0.1 mol) | Methanol | Reflux | 2 days | 44.8:40.3 | |

EXAMPLE 3

Preparation of methyl E-2-(2-methylphenoxymethyl)phenylglyoxylate oxime

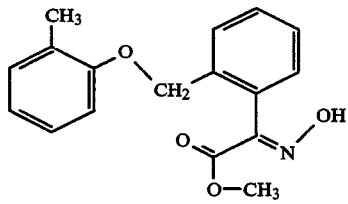

56.8 g (0.2 mol) of methyl 2-(2-methylphenoxymethyl)phenylglyoxylate and 15.2 g (0.22 mol) of hydroxylammonium chloride in 67.5 ml of methanol are refluxed for 6.5 hours. The resulting mixture (of E- and Z-oximes) is cooled to 0° C. and 14.2 g (0.39 mol) of hydrogen chloride are passed in, and the mixture is then stirred at 25° C. for 5 hours. The solvent is removed by distillation under reduced pressure, the residue is taken up in diethyl ether, and the solution is washed with water, dried over sodium sulfate and evaporated to dryness. 55.3 g of solid E isomer (melting point 115° C.) are obtained.

EXAMPLE 4

15.7 g of a mixture containing 30% of methyl 2-(2-methylphenoxymethyl)phenylglyoxylate methylnitrone and 42% of methyl E-2-(2-methylphenoxymethyl)phenylglyoxylate O-methyl oxime are mixed with 70 ml of methanol. 0.9 g (0.05 mol) of water is added and then 3.7 g (0.1 mol) of hydrogen chloride are passed in. The mixture is stirred at 65° C. for 1 hour. The solvent is removed by distillation, the residue is taken up in ethyl acetate, and the organic solution is extracted twice with water, dried over sodium sulfate and distilled to remove solvent. HPLC analysis of the 14.6 g of residue shows that the methylnitrone has been completely converted into methyl 2-(2-methylphenoxymethyl)phenylglyoxylate and methyl 2-(2-methylphenoxymethyl)phenylglyoxylate dimethyl ketal (in the ratio 3:1).

EXAMPLE 5 a) 1.5 g (4.8 mmol) of methyl 2-(2-methylphenoxymethyl)phenylglyoxylate methylnitrone are dissolved in 20 ml of methanol, and 3.8 g (5.5 mmol) of hydroxylamine hydrochloride are added. The mixture is then refluxed for 4 h and subsequently methanol is stripped off. The residue is taken up in 50 ml of diethyl ether, the solution is washed with 2×20 ml of water, the phases are separated and the organic phase is concentrated. Yield: 1.1 g (3.6 mmol, 75%) of methyl 2-(2-methylphenoxymethyl)phenylglyoxylate oxime (isomer mixture).

b) 1.5 g (4.8 mmol) of methyl 2-(2-methylphenoxymethyl)phenylglyoxylate methylnitrone are dissolved in 20 ml of methanol, and 4.6 g (5.5 mmol) of methoxylamine hydrochloride are added. The mixture is heated to reflux for 4 h and subsequently methanol is stripped off. The residue is taken up in 50 ml of dichloromethane, the solution is washed 2× with 20 ml of water, the phases are separated, and the organic phase is concentrated. Yield: 0.9 g (60%) of methyl 2-(2-methylphenoxymethyl) phenylglyoxylate O-methyl oxime (isomer mixture).

We claim:
1. A process for preparing E-oxime ethers of the formula I

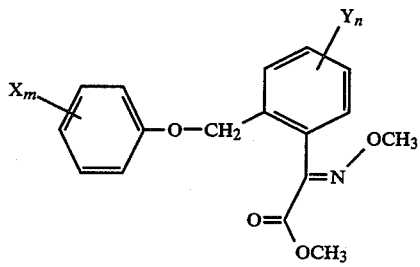

where
  X and Y are identical or different and each is halogen, $C_1$–$C_4$-alkyl, $C_1$–$C_4$-alkoxy, trifluoromethyl, or 1-$C_1$–$C_5$-alkyl ($C_2$–$C_5$-alkenyl) hydroxyimino-$C_1$–$C_5$-alkyl ($C_2$–$C_5$-alkenyl) and 1-$C_1$–$C_5$-alkyl(-$C_2$–$C_5$-alkenyl)hydroxyimino,
  m is an integer from 0 to 4,
  n is an integer from 0 to 3, which comprises
    (1) preparing an E-oxime of the formula IIa

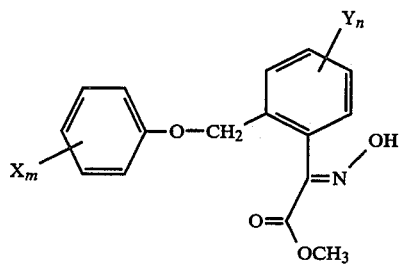

where the substituents have the meanings specified above, which comprises treating a mixture of an E-oxime of the formula IIa and the corresponding Z-oxime in a one-phase system with an acidic catalyst in an organic diluent to prepare said E-oxime,
    (2) converting said E-oxime of the formula IIa with a base in the presence of an organic diluent into the corresponding salt and
    (3) reacting said corresponding salt with a methylating agent of the formula $$CH_3X \qquad\qquad III$$

where

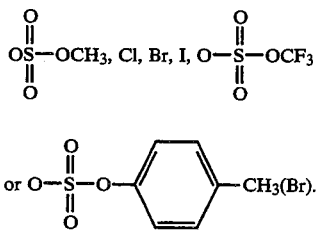

2. A process as claimed in claim 1, wherein a low molecular weight alcohol is used as organic diluent.

3. A process as claimed in claim 1, wherein gaseous hydrogen chloride is used as catalyst and methanol is used as organic diluent.

4. A process as claimed in claim 1, wherein from 0.01 to 5 mole equivalents of gaseous hydrogen chloride (based on the mixture) and methanol are used.

* * * * *